United States Patent [19]

Valentine et al.

[11] Patent Number: 5,609,883
[45] Date of Patent: Mar. 11, 1997

[54] COMPRESSED TABLET TRANSITORY LUBRICANT SYSTEM

[75] Inventors: William Valentine; William K. Valentine, both of Lawrenceville, Ga.

[73] Assignee: Advanced Technology Pharmaceuticals Corporation, Lawrenceville, Ga.

[21] Appl. No.: 307,922

[22] Filed: Sep. 16, 1994

[51] Int. Cl.$^6$ .................................................. A61K 9/46
[52] U.S. Cl. ........................ 424/464; 424/465; 424/466; 424/488
[58] Field of Search .................................. 424/464, 465, 424/466, 488

[56] References Cited

U.S. PATENT DOCUMENTS

| | | | |
|---|---|---|---|
| 4,004,036 | 1/1977 | Schmitt | 426/285 |
| 4,091,091 | 5/1978 | Terrill | 514/509 |
| 4,684,534 | 8/1987 | Valentine | 427/3 |
| 4,810,307 | 3/1989 | Caton | 127/63 |
| 4,837,031 | 6/1989 | Denton | 424/464 |
| 4,898,736 | 2/1990 | Katdare | 424/465 |
| 4,906,478 | 3/1990 | Valentine et al. | 424/682 |
| 5,019,398 | 5/1991 | Daste | 424/480 |
| 5,021,242 | 6/1991 | Romer et al. | 424/436 |
| 5,064,651 | 11/1991 | Mochizuki et al. | 424/440 |
| 5,069,910 | 12/1991 | Kovacic et al. | 424/464 |
| 5,073,384 | 12/1991 | Valentine et al. | 424/465 |
| 5,082,667 | 1/1992 | Van Scoik | 424/469 |
| 5,084,277 | 1/1992 | Greco et al. | 424/433 |
| 5,275,822 | 1/1994 | Valentine et al. | 424/489 |
| 5,427,799 | 6/1995 | Valentine et al. | 424/451 |

FOREIGN PATENT DOCUMENTS 0131485  7/1983  European Pat. Off. .

OTHER PUBLICATIONS

Remington's Pharmaceutical Sciences Martin (13th Edition, 1965) "Molded Tablets or Tablet Triturates ", (TT) pp. 579–581.

*Primary Examiner*—Amy Hulina
*Attorney, Agent, or Firm*—DeLio & Peterson, LLC

[57] ABSTRACT

A method is provided for making fast dissolving storage stable tablets by compression on standard high speed tablet production machinery wherein the formulation contains a carbohydrate having a special particle size and/or structure, in combination with controlled amounts of a transitory liquid as a lubricant, which liquid is removed following compression.

13 Claims, No Drawings

COMPRESSED TABLET TRANSITORY LUBRICANT SYSTEM

BACKGROUND OF THE INVENTION

1. Field of the Invention

The present invention relates to a process for the manufacture of fast dissolving compressed tablets with enhanced liquescent character and, in particular, to the use of a transitory liquid lubricant to produce fast dissolving compressed tablets.

2. Description of Related Art

It is desirable to provide liquescent or meltable tablets containing active ingredients which can be readily chewed or alternatively allowed to melt in the oral cavity. Such tablets have particular appeal for those consumers unable to swallow or chew conventional compressed tablets.

Prior to the present invention, it has been known to prepare tablet triturates which are soluble but very friable. The triturates are prepared by dampening a blend of a drub and diluent with ethyl alcohol containing varying quantities of water, forcing the dampened mass into holes in a forming plate, then pushing the mass out of the molds by push pins, and drying in ovens or heated tunnels. The finished tablet triturates are usually limited in size to about 250 mg and breakage from the ejection push pins is a problem as the size of the tablet is increased.

Tablet triturates formed on production equipment have an extremely high loss from tablet breakage with reject numbers running as high as 25–30%.

U.S. Pat. No. 4,684,534 describes a quick-liquefying chewable tablet characterized by a harder outer shell which inhibits penetration of liquid into the interior of the tablet, and a softer interior which quickly liquefies when the tablet shell is broken into pieces and contacted by a liquid. All of the examples in the patent describe tablets formed employing a relatively large amount of a non transitory metallic stearate lubricant. The tablet formulations described in the body of the patent are capable of improvement by substituting the liquid transitory lubricant of the present invention for the metallic stearate or other fat based lubricants disclosed in the patent. This patent is hereby incorporated by reference.

U.S. Pat. No. 4,810,307 describes a method for making a starch hydrolysate particle having increased bulk density and dissolution rate properties. Commercially available maltodextrin powder is subjected to roll compaction utilizing an amount of a liquid such as ethyl alcohol, acetone, hexane, cyclohexane, methyl ethyl ketone, etc. to form a damp powder blend. The blend is compacted between a pair of compacting rollers to form a sheet of material composed of formerly discrete maltodextrin particles crushed together with the liquid. The sheet is then broken into small particles and the remaining solvent removed by drying. The resulting particles are non-spherical and appear crystalline.

Maltodextrin agglomerates, compacts, or spray dried powders are unacceptable as the main excipient in a chewable tablet because the maltodextrin is a polymer and as such does not have the dissolution rate of a simple sugar such as mannitol or dextrose. The polymeric maltodextrin goes through a high viscosity stage in its dissolution and will stick to the teeth when chewed and in addition will demonstrate a dry then gelatinous mouth feel when chewed or sucked.

Bearing in mind the problems and deficiencies of the prior art, it is a primary object of the present invention to provide a method for making tablets by compression utilizing a transitory liquid lubricant and a special tablet formulation.

It is another object of the present invention to provide a method for making tablets by compression which are liquescent, meltable, or effervescent on conventional tablet compression machinery by the use of a transitory liquid lubricant.

It is yet another object of the present invention to provide a method for making tablets by compression which are liquescent, meltable or effervescent on conventional high speed tablet compression machinery containing therapeutic quantities of pharmacologically active substances.

It is still another object of the present invention to provide a method for the manufacture of an effervescent tablet on conventional tablet compression machinery by utilizing a transitory liquid lubricant that is removed after compression and which substantially obviates the need for special water soluble lubricants in order to ensure complete tablet dissolution following effervescence.

Another object of the invention is to provide tablets prepared by the method of the invention.

Still another object of the invention is to provide formulations which may be compressed into tablets.

Other objects and advantages of the invention will be readily apparent from the following description.

SUMMARY OF THE INVENTION

The present invention discloses a method for making tablets by compression on standard high speed tablet production machinery wherein the necessary punch face and die wall lubrication is effected by the use of a formulation containing a material having a special particle size and/or structure, preferably a carbohydrate, in combination with controlled amounts of a transitory liquid which liquid is removed, i.e., by drying, following compression. Effervescent tablets may also be made utilizing the method of the invention and are primarily designed to rapidly dissolve in water, prior to consumption and may be dissolved in the mouth fluids if the effervescent action is mild. The compressed tablets of this invention therefore have particular appeal for those consumers unable to swallow or chew conventional compressed tablets.

It has been found that formulations containing materials such as dextrose, having a particular structure (agglomerated) and/or particle size greater than about 100 mesh when used with controlled amounts of a liquid such as alcohol up to about 5% by weight of the formulation, may be compressed on standard tablet production machinery to produce tablets said tablets being particularly useful for fast dissolution in the mouth and/or effervescent tablets.

The preferred materials are carbohydrates and particularly preferred is dextrose, which has been agglomerated according to U.S. Pat. No. 4,684,534. As set forth in the patent, minor amounts of 1–10% by weight of binder materials may be used to form the agglomerate such as corn syrup solids, dextrose, sucrose, polyvinylpyrollidone, cooked starch paste and maltodextrin.

The present invention further describes a method for fabricating a lubricantless, fast dissolving, relatively large, packageable, storage stable, meltable, liquescent, or effervescent tablet. Said tablet being capable of carrying medicaments and/or flavorants that are quickly and effectively released.

Such improved compressed dose form properties have been sought in order to provide those subjects unable to swallow or chew conventional tablets with a more meltable liquescent or effervescent unit dose form.

DESCRIPTION OF THE PREFERRED EMBODIMENT(S)

A tablet according to the present invention is compressed from a soluble, preferably carbohydrate, particle or agglomerate usually containing an active substance and a transitory liquid lubricant. Following removal of the transitory lubricant, the resulting lubricantless tablets are of sufficient hardness to resist damage during packaging and yet retain their desired properties such as their liquescent and/or effervescent character.

The materials which may be employed in the invention preferably comprise carbohydrates selected from the group consisting of dextrose, fructose, sucrose, lactose, maltose, xylose, mannitol and mixtures thereof. If an agglomerate is to be used a water soluble binder to form the agglomerate may be selected, for example, from the group consisting of maltodextrin, corn syrup solids, dextrose, sucrose, polyvinylpyrollidone and cooked starch paste. The quantity of water-soluble binder is in the range of from about 1 percent to about 10 percent by weight of the agglomerate (without active ingredient), and preferably from about 1 percent to about 5 percent, with the carbohydrate-based particles comprising from about 90 percent to about 99 percent by weight of the agglomerate (without active ingredient). Dextrose or a coagglomerate including dextrose is preferred because it is able to be adequately lubricated with less alcohol, dried with less energy expenditure and the final tablet is characterized by a rapid tack free dissolution.

While agglomerates are preferred for many of the desired tablet products, both agglomerates and particles may be employed with the proviso that substantially all of the non-active material of the formulation be greater than about 100 mesh, preferably, 50, 80, and most preferably 90, 95% or more of the material used. A preferred particle size range is between about −20 mesh to +100 mesh (about 150 microns to about 800 microns) and preferably −20 mesh to +88 mesh.

It is believed that the agglomerates from which the tablets are made have an open pore or duct-like structure and a resulting large surface area to volume ratio which causes the particles to readily dissolve on contact with small amounts of any liquid, including saliva, in which the agglomerate is at least partially soluble.

While not wishing to be limited by an particular theory, it is believed that the liquescent, or effervescent character of the tablets of the present invention owe their enhanced performance to the lack of the water sealant effect of either a conventional water repellent fat based lubricant, or a conventional water resisting soluble lubricant and that the removal of the transitory lubricant following compression results in a tablet surface that while hard, is extremely dissolution labile. The liquescent character of a tablet of the present invention is readily demonstrated by the rapid liquefaction when a tablet is placed in the mouth or when a tablet is dissolved in water by effervescent action.

The term "active ingredient" is used herein in a broad sense and encompasses any material which can be carried by or entrained by the particle or by/in the agglomerate. For example, an active ingredient can be a pharmaceutical such as an antacid, analgesic or drug; or a flavor, breath sweetener, vitamin, dietary supplement, or nutrient; or the like and combinations thereof. Active ingredients include but are not limited to; insoluble metal and mineral hydroxides, carbonates, acidulents, biocarbonates, oxides, and salts thereof; active drugs, adsorbates of active drugs or coated active drugs.

The invention is broadly applicable to making a wide variety of tablets including but not limited to, antacid tablets, cough medicine tablets, sore throat tablets, breath freshener tablets, vitamin tablets, calcium tablets, dietary supplement and nutrient tablets, laxative tablets, cold tablets, antipyretic tablets, anti-diarrhea tablets, reducing tablets, pain reliever tablets, sleeping tablets, and many prescription and non-prescription drug and pharmaceutical tablets.

The agglomerate can be formed from the carbohydrate particles and the water-soluble binder without an active ingredient, and the active ingredient and agglomerate can be mixed to cause the active ingredient to be entrained by and dispersed in the agglomerate.

As described in U.S. Pat. No. 4,684,534, one process for making the carbohydrate-based agglomerate comprises the steps of forming a fluidized bed of the carbohydrate particles, intermittently spraying a solution of the water soluble binder in a droplet size of from about 20 microns to about 100 microns into the fluidized bed so as to cause intimate commingling of solution and carbohydrate particles and adhesion together of carbohydrate particles to form agglomerated particles, drying the particles in the fluidized bed between intermittent sprayings, and continuing spraying and drying until the desired amount of solution has been sprayed into the bed. Thereafter, the agglomerated particles are dried to a desired moisture content or the equilibrium moisture content. The amount of liquid binder solution sprayed corresponds to a binder content in the agglomerate of from about 1 percent to about 10 percent by weight of the agglomerate (excluding active ingredient). The carbohydrate-based agglomerate, (or particle) and an active ingredient are mixed, preferably in a low shear blender, in any suitable proportions by weight of the finished formulation (including active ingredient) such as, about 50 percent to about 90 percent agglomerate and about 10 percent to about 50 percent active ingredient.

The liquid lubricant of the invention is also mixed together with the agglomerate and the active ingredient, if any, in the proportion of up to about 5 percent, preferably 1–4%, and most preferably 2–3.5% by weight of the final formulation to be tabletted (including active ingredient). Flavors and other adjutants can also be mixed with the agglomerate and active ingredient to produce the final formulation.

Suitable liquids which may be employed as the lubricant may be selected from normally fluid and volatile alcohols and the like. Particularly preferred are the alcohols such as methyl, ethyl and propyl with ethyl alcohol (95% alcohol–5% water by weight) being preferred because of its demonstrated effectiveness and non-toxic properties.

An agglomerate including an entrained active ingredient can be formed by the process described above wherein the active ingredient is mixed with the carbohydrate particles and a fluidized bed is formed of this mixture. When the agglomerate is formed with an entrained active ingredient, the active ingredient can comprise up to about 75 percent of the weight or more of the finished agglomerate (including active ingredient). Physical evidence shows that agglomerates formed with an active ingredient have a structure similar to that of agglomerates formed without an active ingredient.

A process for making a tablet from the finished carbohydrate-based formulations described above including up to about 5 percent of a liquid lubricant, comprises compressing the formulation in conventional tablet-forming apparatus to a hardness sufficient to generate a handleable tablet. The compression is followed by drying in order to remove the liquid lubricant and allow the concomitant hardening of the tablet.

For the materials described herein, it has been found that tablets compressed to a hardness of from about 1 kp to about 5 kp or more, preferably about 1.5 kp to about 3 kp have an interior which for agglomerate formulations essentially retain the physical structure of the agglomerate. It has also been found that these tablets upon drying (removal of remaining liquid lubricant) increase in hardness to provide tablets which are easily handled without breakage, yet which are extremely dissolution labile. In general, the hardness of the tablet will increase up to about 5 fold or more upon drying, e.g., 5–10 kp. The term "kp" means kilo pounds, a well known unit of force for expressing hardness or crushing strength of pharmaceutical tablets. Values are obtained using such testers as a Schleuniger Tablet Hardness Tester and Herberlein Tablet Hardness Tester.

Pressures applied to compress the agglomerates into tablets having a hardness of from about 1 kp to about 5 kp were found to be in the order of about 5–10% percent of the pressures ordinarily used to make tablets.

Standard tableting machinery is well known in the art and the basic mechanical unit in all tablet compression equipment includes a lower punch which fits into a die from the bottom and an upper punch, having a head of the same shape and dimensions, which enters the die cavity. The tablet is formed by pressure applied on the punches and is subsequently ejected from the die. The weight of the tablet is determined by the volume of the material which fills the die cavity. Therefore, the ability of the granulation to flow freely into the die is important in insuring a uniform fill, as well as the continuous movement of the granulation from the source of supply or feed hopper. If the tablet granulation does not possess cohesive properties, the tablet after compression will crumble and fall apart on handling. As the punches must move freely within the die and the tablet must be readily ejected from the punch faces, the material must have a degree of lubrication to minimize friction and to allow for the removal of the compressed tablets.

For increased production the standard rotary machines offer the greatest advantages. A head carrying a number of sets of punches and dies revolves continuously while the tablet granulation runs from a feed hopper, through a feed frame, and into the dies placed in a large, steel plate revolving under it. This method promotes a uniform fill of the die and therefore an accurate weight control for the tablets. Compression takes place as the upper and lower punches pass between a set of rollers. This action produces a high tonnage pressure squeezing effect on the material in the die cavity. When compression is complete, the lower punch raises and the tablet is ejected as it strikes an ejection plate and exits from the die table and the machine. Because of the high operational speed of a rotary tablet press and the relatively large surface area involved, adequate internal lubrication of the fast moving parts becomes essential and extremely critical.

For example, the total surface area requiring lubrication on a rotary tablet press is rather large when compared for example to the small nip angle of a rotary compactor described in U.S. Pat. No. 4,810,307.

In the practice of the present invention, coated drugs such as, for example, coated acetaminophen, can readily be incorporated into the tablet without disrupting the coating because of the relatively low compression force used to compress the tablet and the resultant concomitant rapid dissolution of the dose form without mastication.

The following examples will serve to further illustrate the details for the preparation of tablets compressed on standard compression equipment with the necessary die and punch lubrication supplied by a transitory liquid lubricant. The invention which is set forth in the foregoing disclosure is not to be construed as being limited either in spirit or scope by these examples.

All the agglomerated materials were prepared according to U.S. Pat. No. 4,684,534 and had a particle size range of about +20 to +100 mesh. The ethyl alcohol was 5% by weight water.

EXAMPLE #1

| Agglomerated dextrose | 100 g |
| Ethyl Alcohol | 2 cc |

Blend the agglomerated dextrose with ethanol and mix well. The tablets were pressed without problems on 9/16" flat faced beveled edge punches at a hardness of 1.5 Kp and were dried at ambient temperature, 37° C., and 45° C. until dry (1 hr.) Tablet hardness increased to 5 Kp. All tablets demonstrated liquescent melt away character.

EXAMPLE #2

| 53% Calcium carbonate/dextrose monohydrate/ maltodextrin co-agglomerate (2% maltodextrin) | 640 g |
| Dextrose monohydrate/maltodextrin co-agglomerate (5% maltodextrin) | 360 g |
| Ethyl Alcohol | 40 cc |

Blend the agglomerates and blend with the ethanol and mix well. The tablets were pressed without problems on 9/16" flat faced beveled edge, punches at a hardness of 1.5–2.0 kp and dried at 37° C. for 1 hour. The tablets increased in hardness to about 5–6 Kp. The tablets demonstrated the desired liquescent melt away character and were harder on the outside than on the inside as described in U.S. Pat. No. 4,684,534.

EXAMPLE #3

| Dextrose monohydrate/maltodextrin co-agglomerate (5% maltodextrin) | 984 g |
| 33.3% Coated chlorpheniramine maleate (VEI) | 12 g |
| Spray dried lemon flavor | 4 g |
| Ethyl Alcohol | 40 cc |

Blend the dextrose/maltodextrin agglomerate, coated chlorpheniramine maleate, and the spray dried lemon flavor in a Hobart type planetary mixer until uniform. Add the ethanol and blend until a uniformly damp granule has been formed.

The damp flowable granular blend was transferred to a tablet press and pressed at 510 mg per tablet and a hardness of 1–1.5 Kp on 7/16 standard concave punches. No compression problems were encountered. The biconvex tablets were dried at room temperature for one hour and the hardness rechecked and found to be at 5–6 Kp. The tablets demonstrated the desired liquescent characteristics and were harder on the outside than on the inside as described in U.S. Pat. No. 4,684,534.

EXAMPLE #4

| | |
|---|---|
| Dextrose monohydrate/maltodextrin co-agglomerate (5% maltodextrin) | 845.6 g |
| 33.3% Coated chlorpheniramine maleate | 3.4 g |
| 33.3% Coated pseudoephedrine HCl | 50.0 g |
| 10% Dextromethorphan HBr magnesium trisilicate adsorbate | 56.0 g |
| Spray dried lemon flavor | 45.0 g |
| Ethyl Alcohol | 44 cc |

Blend the dextrose/maltodextrin co-agglomerate, coated chlorpheniramine maleate, coated pseudoephedrine HCL dextromethorphan HBr adsorbate, and the lemon flavor in a Hobart type planetary mixer until uniform. Add the ethanol and mix until a uniformly damp granulation has been formed. The damp granulation was pressed on a tablet press using 9/16" flat faced beveled edged punches at a weight of 900 mg and a hardness of 1.5–2.0 Kp. The tablets were dried at 37° C. for 30 minutes or until the ethanol had been removed. The finished tablets increased in hardness to 5–6 Kp and demonstrated the desired enhanced liquescent characteristics and additionally were harder on the outside than on the inside as described in U.S. Pat. No. 4,684,534.

EXAMPLE #5

| | |
|---|---|
| Dextrose monohydrate/maltodextrin co-agglomerate (5% maltodextrin) | 1865.0 g |
| Calcium carbonate (Vercode 150) | 1125.0 g |
| Spray dried lemon flavor | 12.0 g |
| Ethyl alcohol | 120 cc |

The dextrose/maltodextrin co-agglomerate, calcium carbonate and the spray dried lemon flavor were blended and then the ethyl alcohol was added and mixed until uniformly damp and granular. A standard tablet press with 9/16" flat faced beveled edged punches was used to press 500 tablets at 1.5–2.0 Kp at a weight of 1400 mg/tablet. The tablets were dried at 37° C., 45° C. and at room temperature. Approximately 500 tablet portions of the base granulation were compressed at 30 minute intervals until the granulation was exhausted (2 hours). No compression problems were experienced. The three drying conditions were repeated at each compression time interval.

The transitory lubricant was effective in lubricating the punch faces and die walls throughout the compression trial (i.e. 2 hours). The transitory lubricant was at or near the surface of the tablet following compression and was readily removed at all drying conditions. The speed with which the transitory lubricant was removed was accelerated by an increase in drying temperature and/or an increase in air flow.

The finished tablets had a hardness of 6–8 Kp and demonstrated the desired enhanced liquescent characteristics and were, additionally, harder on the outside than on the inside as described in U.S. Pat. No. 4,684,534.

EXAMPLE #6

| | |
|---|---|
| Anhydrous dextrose agglomerate | 84.5 g |
| Calcium carbonate (vercode 150) | 10.0 g |
| Citric acid, anhydrous | 5.0 g |
| Spray dried lemon flavor | 0.5 g |
| Ethyl alcohol | 4.0 cc |

The materials were blended until uniform and then dampened with the alcohol. Tablets were then compressed on a tablet machine at 1000 mg at 2–2.5 Kp. Following drying at 37° C., the hardness increased to 4–5 Kp and the tablets possessed the desired liquescent characteristics. The tablets were harder on the outside than on the inside as described in U.S. Pat. No. 4,684,534.

EXAMPLE #7

The method of Example #6 was repeated with the addition of 0.31 g of coated 33% chlorpheniramine maleate. The finished dried tablets exhibited the same attributes as EXAMPLE #6.

EXAMPLE #8

| | |
|---|---|
| Anhydrous dextrose agglomerate | 84.0 g |
| Sodium bicarbonate | 5.0 g |
| Citric acid anhydrous | 5.0 g |
| 33% pseudoephedrine HCl | 4.5 g |
| Spray dried lemon flavor | 0.8 g |
| 33% chlorpheniramine maleate | 0.7 g |
| Ethyl alcohol | 4.0 cc |

The materials were blended in a Hobart type planetary mixer until uniform. The alcohol was added and mixed until a damp flowable granule was formed. Tablets were compressed on 9/16– flat faced beveled edged tooling at a hardness of 1.5–2.0 Kp. Following drying to remove the volatile transitory lubricant, the tablet hardness increased to 5–6 Kp. The finished tablets had mild effervescence, rapid dissolution and enhanced liquescence. The finished tablets were harder on the outside than on the inside as described in U.S. Pat. No. 4,684,534.

EXAMPLE #9

| | |
|---|---|
| Agglomerated anhydrous dextrose | 50 g |
| Citric acid, anhydrous | 25 g |
| Sodium bicarbonate | 25 g |
| Ethyl alcohol | 3.5 cc |

The ingredients were blended in a Hobart type planetary mixer and mixed until uniform. The alcohol was added and the product remixed until a uniformly damp flowable granule was formed. The uniformly damp flowable granulation was compressed on a tablet press fitted with ¾" standard concave tooling. The 2 g biconvex tablets were compressed at a hardness of 3.0–3.5 Kp and dried for 10 minutes in moving 37° C. air. The dried tablets had a hardness of 8°10 Kp and a smooth surface appearance. Examination of the tooling following compression indicated thorough and complete lubrication during compression.

The tablets effervesced completely in 200 ml of cold tap water in 1.0 minute. There was no visible residue on the surface of the water nor on the side of the beaker.

While the invention has been described with reference to specific embodiments, it will be recognized by those skilled in the art that variations are possible without departing from the spirit and scope of the invention, and that it is intended to cover all such variations of the materials disclosed herein for the purpose of illustration which do not constitute departure from the spirit and scope of the invention.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

While the invention has been illustrated and described in what are considered to be the most practical and preferred embodiments, it will be recognized that many variations are possible and come within the scope thereof, the appended claims therefore being entitled to a full range of equivalents.

Thus, having described the invention, what is claimed is:

1. A method for making fast dissolving tablets on standard compression tabletting machinery comprising a die cavity, an upper punch and a lower punch the method comprising:

forming a formulation to be tabletted wherein at least one of the ingredients in the formulation is a carbohydrate in an amount of at least 50% by weight of the formulation and greater than 50% of the carbohydrate has a particle size greater than about 100 mesh;

using as a lubricant in the formulation a liquid material selected from the group consisting of alcohols, and mixtures thereof in an amount of about 1–5% by weight of the formulation;

feeding the formulation into the die cavity;

compressing the formulation using the standard compression tabletting machinery to form a compressed tablet, the compressed tablet having a hardness above about 1 Kp;

ejecting the compressed tablet from the die cavity; and removing the lubricant from the compressed tablet to form the fast dissolving tablet.

2. The method of claim 1 wherein the lubricant is ethyl alcohol.

3. The method of claim 2 wherein greater than 90% of the carbohydrate has a particle size greater than about 100 mesh.

4. A method for making fast dissolving tablets on standard compression tabletting machinery comprising a die cavity, an upper punch and a lower punch the method comprising:

forming a formulation to be tabletted wherein at least one of the ingredients in the formulation is an agglomerated carbohydrate in an amount of at least 50% by weight of the formulation and greater than 50% of the agglomerated carbohydrate has a particle size greater than about 100 mesh;

using as a lubricant in the formulation a liquid material selected from the group consisting of alcohols, and mixtures thereof in an amount of about 1–5% by weight of the formulation;

feeding the formulation into the die cavity;

compressing the formulation using the standard compression tabletting machinery to form a compressed tablet, the compressed tablet having a hardness above about 1 Kp;

ejecting the compressed tablet from the die cavity; and removing the lubricant from the compressed tablet to form the fast dissolving tablet.

5. The method of claim 4 wherein the agglomerate is dextrose wherein greater than 50% of the agglomerate has a particle size greater than about 100 mesh.

6. The method of claim 5 wherein the dextrose agglomerate has about 1–10% by weight of a binder.

7. The method of claim 4 wherein the alcohol is ethyl alcohol.

8. The method of claim 5 wherein the alcohol is ethyl alcohol.

9. The method of claim 1 wherein the formulation contains an active ingredient.

10. The method of claim 4 wherein the carbohydrate is an agglomerated carbohydrate and greater than 90% of the carbohydrate has a particle size greater than about 100 mesh.

11. The method of claim 10 wherein the agglomerate is dextrose.

12. The method of claim 11 wherein the dextrose agglomerate contains about 1–10% by weight of a binder.

13. The method of claim 4 wherein the formulation contains an active ingredient.

\* \* \* \* \*

UNITED STATES PATENT AND TRADEMARK OFFICE
CERTIFICATE OF CORRECTION

PATENT NO. : 5,609,883
DATED : March 11, 1997
INVENTOR(S) : William Valentine

It is certified that error appears in the above-identified patent and that said Letters Patent is hereby corrected as shown below:

Column 6, Line 14: please delete "+20" and insert - - -20 - -.

Column 8, Line 35: please delete "9/16-" and insert - - 9/16" - -.

Column 8, Line 58: please delete 8°10 and insert - - 8-10 - -.

Signed and Sealed this

First Day of July, 1997

Attest:

BRUCE LEHMAN

Attesting Officer

Commissioner of Patents and Trademarks